(12) United States Patent
Wahlstrand et al.

(10) Patent No.: US 7,616,995 B2
(45) Date of Patent: Nov. 10, 2009

(54) VARIABLE RECHARGE DETERMINATION FOR AN IMPLANTABLE MEDICAL DEVICE AND METHOD THEREFORE

(75) Inventors: Carl D. Wahlstrand, Lino Lakes, MN (US); Robert M. Skime, Coon Rapids, MN (US); Erik R. Scott, Maple Grove, MN (US); Craig L. Schmidt, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 461 days.

(21) Appl. No.: 11/414,156

(22) Filed: Apr. 28, 2006

(65) Prior Publication Data

US 2007/0255354 A1 Nov. 1, 2007

(51) Int. Cl.
*A61N 1/378* (2006.01)
(52) U.S. Cl. .......................................... 607/34; 607/29
(58) Field of Classification Search .................... 607/29, 607/34
See application file for complete search history.

(56) References Cited

U.S. PATENT DOCUMENTS

| | | | |
|---|---|---|---|
| 4,134,408 A | 1/1979 | Brownlee et al. |
| 4,276,883 A | 7/1981 | McDonald et al. |
| 4,612,934 A | 9/1986 | Borkan |
| 5,344,431 A | 9/1994 | Merritt et al. |
| 5,370,668 A | 12/1994 | Shellton et al. |
| 5,391,193 A | 2/1995 | Thompson |
| 5,402,070 A | 3/1995 | Shelton et al. |
| 5,411,537 A | 5/1995 | Munshi et al. |
| 5,733,313 A | 3/1998 | Barreras, Sr. et al. |
| 5,735,887 A | 4/1998 | Barreras, Sr. et al. |
| 5,769,877 A | 6/1998 | Barreras, Sr. et al. |
| 5,807,397 A | 9/1998 | Barreras |
| 5,869,970 A | 2/1999 | Palm et al. |
| 5,876,425 A | 3/1999 | Gord et al. |
| 5,941,906 A | 8/1999 | Barreras, Sr. et al. |
| 5,973,497 A | 10/1999 | Bergk et al. |
| 5,983,137 A | 11/1999 | Yerkovich |
| 6,016,448 A | 1/2000 | Busacker et al. |
| 6,067,474 A | 5/2000 | Schulman et al. |
| 6,141,583 A | 10/2000 | Pape et al. |
| 6,154,675 A | 11/2000 | Juran et al. |

(Continued)

FOREIGN PATENT DOCUMENTS

EP  1 424 098 A1  6/2004

(Continued)

OTHER PUBLICATIONS

International Search Report for PCT/US2007/001728.

*Primary Examiner*—Carl H Layno
*Assistant Examiner*—Brian T Gedeon
(74) *Attorney, Agent, or Firm*—IPLM Group, P.A.

(57) ABSTRACT

Implantable medical device adapted to provide a therapeutic output to a patient. A therapy module, operatively coupled to a battery, is adapted to provide the therapeutic output. A control circuit provides an action indicative of recharging the battery when the voltage of the battery reaches a recharge voltage wherein the recharge voltage is varied as the battery ages. Also a method of providing a therapeutic output to a patient using an implantable medical device having a battery having a voltage. An action indicative of recharging the battery is provided when the voltage of the battery reaches a recharge voltage. The recharge voltage is varied as the battery ages.

21 Claims, 14 Drawing Sheets

U.S. PATENT DOCUMENTS

| | | |
|---|---|---|
| 6,167,309 A | 12/2000 | Lyden |
| 6,304,779 B1 | 10/2001 | Yerkovich |
| 6,377,850 B1 | 4/2002 | Takeuchi et al. |
| 6,453,198 B1 | 9/2002 | Torgerson et al. |
| 6,516,227 B1 | 2/2003 | Meadows et al. |
| 6,543,883 B1 | 4/2003 | Torgerson et al. |
| 6,553,263 B1 | 4/2003 | Meadows et al. |
| 6,631,293 B2 | 10/2003 | Lyden |
| 6,654,640 B2 | 11/2003 | Lyden |
| 6,671,552 B2 | 12/2003 | Merritt et al. |
| 6,687,543 B1 | 2/2004 | Isaac et al. |
| 6,771,047 B1 | 8/2004 | Ogonowsky |
| 6,820,019 B1 | 11/2004 | Kelly et al. |
| 6,937,891 B2 * | 8/2005 | Leinders et al. ............... 607/2 |
| 7,450,991 B2 | 11/2008 | Smith et al. |
| 2001/0034541 A1 | 10/2001 | Lyden et al. |
| 2003/0191504 A1 | 10/2003 | Meadows et al. |
| 2003/0195581 A1 | 10/2003 | Meadows et al. |
| 2004/0024426 A1 | 2/2004 | Lyden |
| 2004/0073264 A1 | 4/2004 | Lyden |
| 2004/0138647 A1 | 7/2004 | Osorio et al. |
| 2004/0158296 A1 | 8/2004 | Greatbatch et al. |
| 2004/0162592 A1 | 8/2004 | Betzold et al. |
| 2004/0222768 A1 | 11/2004 | Moore et al. |
| 2005/0077872 A1 | 4/2005 | Single |
| 2005/0156577 A1 | 7/2005 | Sully |

FOREIGN PATENT DOCUMENTS

| | | |
|---|---|---|
| EP | 0 999 874 B1 | 9/2004 |
| EP | 1 610 437 A | 12/2005 |
| WO | WO 96/20754 | 7/1996 |
| WO | WO 96/22811 | 8/1996 |
| WO | WO 97/15351 | 5/1997 |
| WO | WO 99/06108 | 2/1999 |
| WO | WO 00/24459 | 5/2000 |
| WO | WO 01/08749 A1 | 2/2001 |
| WO | WO 02/09808 A1 | 2/2002 |
| WO | WO 2004/087256 A1 | 10/2004 |

* cited by examiner

VARIABLE RECHARGE DETERMINATION FOR AN IMPLANTABLE MEDICAL DEVICE AND METHOD THEREFORE

FIELD

This invention is generally related to implantable medical devices and, in particular, to rechargeable implantable medical devices.

BACKGROUND

Implantable medical devices are commonly used to treat patients suffering from a variety of medical conditions. Implantable medical devices can be used to treat any number of conditions such as pain, incontinence, movement disorders such as epilepsy and Parkinson's disease, and sleep apnea. Additional therapies appear promising to treat a variety of physiological, psychological, and emotional conditions.

Such implantable medical devices include implantable drug infusion pumps and implantable electrical stimulators. Implantable drug infusion generally infuse a specific amount of a drug contained in a reservoir of the implantable drug infusion pump to the patient in accordance with a scheduled program assigned by a medical professional. Implantable electrical stimulators generally deliver an electrical stimulation to a nerve or other tissue of a patient, e.g., to control pain. In both cases, electrical power may be required to operatively drive the therapeutic componentry associated with each device, e.g., a stepper motor for a drug infusion pump and a pulse generator for an electrical stimulator. In addition, both types of implantable medical devices may also require electrical power for ancillary control and communication circuitry.

An implantable battery is often used as a source of electrical power for an implantable medical device. It is also common to use a rechargeable battery in such an implantable medical device in order to achieve maximum life and small size of the implantable medical device as well as provide robust functions requiring an ample electrical power source. Such implantable medical devices depend upon periodic charging or recharging of the rechargeable battery or batteries in order to maintain continued function of the implantable medical device.

Various techniques and procedures have been established to perform and achieve charging or recharging of an implanted battery of an implantable medical device typically through the use of electromagnetic coupling.

A battery of a typical implantable medical device has a voltage when fully charged. As the battery of the implantable medical is depleted through use the voltage of the battery will typically decline. At a suitable point in time, the battery may then be charged or recharged, e.g., through such electromagnetic coupling, to restore the capacity of the battery.

It is common to utilize the voltage of battery of an implantable medical device as a barometer as to when to charge or to recharge the battery. Typically, the voltage of the battery is monitored and when the voltage of the battery reaches a predetermined voltage, the recharge voltage, the battery is then suitably recharged. The implantable medical device, either alone or in conjunction with an external programmer or control device or monitor, typically signals the user, e.g., the patient, when or following the point in time when the recharge is reached in order that the patient may take appropriate steps to have the battery recharged.

This recharge voltage is typically selected in order to provide the patient with a reasonable useful life, i.e., reasonable functional time between charges, as well as to provide a safety margin or time between the time at which the recharge voltage is reached and a time when the voltage of the battery declines to a point at which the implantable medical device is no longer functional. The time period between the point in time when the recharge voltage is reached and the point in time when the implantable device may no longer function is typically referred to as the compliance period, i.e., the period of time in which the patient should comply with recharging of the battery without risking operation of the device from a low voltage from the battery. The compliance period generally should be long enough to allow the patient a reasonable period of time to accomplish recharging. For example, if special equipment is needed for recharging, then the compliance period should be reasonably long enough to allow the patient in normal situations to obtain and utilize the special equipment needed for recharging.

Generally, the voltage of a fully charged battery when new can be determined within reasonable accuracy. Also, the recharge voltage can be selected for a new battery to achieve a reasonable operational period, i.e., the time period between charges, and also to allow for a reasonable compliance period. It is recognized that a lower recharge voltage will generally provide a longer operational period but a shorter compliance period. The converse is also true. A higher recharge voltage will generally provide a shorter operational period but a longer compliance. Thus, the recharge voltage is generally set at a compromise level to ensure a reasonable operational period and a reasonable compliance period.

However, as the battery of an implanted medical device ages the fully charged voltage will typically decline and, more importantly, the capacity of the battery between its "fully charged" state and its "needs recharging" state may be drastically reduced. For example, a new battery may have a 300 ampere-hour capacity while an aged battery may only have a 30 ampere-hour capacity. Thus an aged but "fully charged" battery may have a lower fully charged capacity and voltage than a "fully charged" battery that is brand new. Thus, the capacity and voltage between the "fully charged" state and the time at which the battery reaches its recharge voltage may be significantly less for an aged battery. As a result, the operational period of an aged battery may be significantly less than the operational period of a brand new battery.

Also, as the battery of an implanted medical device ages the time between the time the battery recharge voltage is reached and the time the lowest operational voltage is reached may also decrease. As a result, the compliance period of an aged battery may be significantly less than the compliance period of a brand new battery.

SUMMARY

As the battery of implanted medical device ages, the operational period or the compliance period of an implanted medical device may also vary.

As the operational period becomes shorter, the patient is required to recharge the battery more frequently. Such more frequent rechargings increase the number of cycles of the battery and may actually cause the battery to age more quickly exacerbating the issue.

As the compliance period becomes shorter, it is more crucial for the patient to promptly recharge the battery of the implanted medical device. In order to compensate for shorter compliance periods with aged batteries, the compliance period for new batteries may be lengthened to account for such shortening ensuring that even under the worst case conditions an adequate compliance period will be maintained.

Unfortunately, maintaining a worst case compliance period may shorten an otherwise longer operational period requiring the patient to recharge the battery more frequently. Such more frequent rechargings increase the number of cycles of the battery and may actually cause the battery to age more quickly also exacerbating the issue.

The recharge voltage may be varied as the battery of an implantable or implanted medical device ages in order to adjust the operational period, the compliance period, or both. For example, the recharge voltage may be decreased over time as the battery of the implantable medical device ages in order to maintain the operational period. Conversely, the recharge voltage may be increased over time as the battery of the implantable medical ages in order to maintain the compliance period. Alternatively, the recharge voltage may be otherwise varied over time in order to achieve other goals related to operational period and/or compliance period or other objectives.

In an embodiment, the present invention provides an implantable medical device adapted to provide a therapeutic output to a patient. A therapy module, operatively coupled to a battery, is adapted to provide the therapeutic output. A control circuit provides an action indicative of recharging the battery when the voltage of the battery reaches a recharge voltage wherein the recharge voltage is varied as the battery ages.

In an embodiment, the recharge voltage is decreased in value as the battery ages.

In an embodiment, the battery has a fully charged capacity which declines as the battery ages and wherein the recharge voltage is varied in order to tend to equalize a value of a difference in voltage between a fully charged voltage and the recharge voltage as the battery ages.

In an embodiment, the difference is maintained to be approximately equal.

In an embodiment, the battery has a fully charged capacity which declines as the battery ages and wherein the recharge voltage is varied in order to tend to equalize an amount of charge imparted to the battery during recharge between a fully charged voltage and the recharge voltage.

In an embodiment, the charge is maintained as approximately equal as the battery ages.

In an embodiment, the action comprises indicating that the battery should be recharged.

In an embodiment, the voltage is varied such that a time between a first recharge of the battery and a second recharge of the battery is made more uniform as the battery ages.

In an embodiment, the time is approximately equal.

In an embodiment, the recharge voltage is increased in value as the battery ages.

In an embodiment, the battery has an off voltage below which the therapy module of the implantable medical device may cease to operate (either completely or partly), wherein the implantable medical device has a patient recharge compliance period commencing upon the action and ending when the voltage of the battery reaches the off voltage and wherein the recharge voltage is varied such that the patient recharge compliance period is maintained to be more uniform as the battery ages.

In an embodiment, the battery has an off voltage below which the therapy module of the implantable medical device may cease to operate (either completely or partly), wherein the implantable medical device has a patient recharge compliance period commencing upon the action and ending when the voltage of the battery reaches the off voltage and wherein the recharge voltage is varied in order to tend to equalize an amount of charge remaining in the battery during the patient recharge compliance period.

In an embodiment, the charge is maintained as approximately equal as the battery ages.

In an embodiment, the recharge voltage is varied in order that the patient recharge compliance period is maintained to be approximately equal as the battery ages.

In an embodiment, the recharge voltage is decreased in value as the battery ages in an early stage of a life of the battery and wherein the recharge voltage is increased in value as the battery ages in a later stage of the life of the battery.

In an embodiment, the recharge voltage is increased in value as the battery ages in an early stage of a life of the battery and wherein the recharge voltage is decreased in value as the battery ages in a later stage of the life of the battery.

In an embodiment, the present invention provides a method of providing a therapeutic output to a patient using an implantable medical device having a battery having a voltage. An action indicative of recharging the battery is provided when the voltage of the battery reaches a recharge voltage. The recharge voltage is varied as the battery ages.

In an embodiment, the recharge voltage in the varying step is decreased in value as the battery ages.

In an embodiment, the battery has a fully charged capacity which declines as the battery ages and wherein the recharge voltage is varied in order to tend to equalize a value of a difference in voltage between a fully charged voltage and the recharge voltage as the battery ages.

In an embodiment, the difference is maintained to be approximately equal.

In an embodiment, the battery has a fully charged capacity which declines as the battery ages and wherein the recharge voltage is varied in order to tend to equalize an amount of charge imparted to the battery during recharge between a fully charged voltage and the recharge voltage.

In an embodiment, the charge is maintained as approximately equal as the battery ages.

In an embodiment, the action step comprises indicating that the battery should be recharged.

In an embodiment, the voltage is varied such that a time between a first recharge of the battery and a second recharge of the battery is made more uniform as the battery ages than it would be with a constant recharge voltage.

In an embodiment, the time is approximately equal.

In an embodiment, the recharge voltage is increased in value as the battery ages.

In an embodiment, the battery has an off voltage below which the therapy module of the implantable medical device may cease to operate properly, wherein the implantable medical device has a patient recharge compliance period commencing upon the action and ending when the voltage of the battery reaches the off voltage and wherein the recharge voltage is varied such that the patient recharge compliance period is maintained to be more uniform as the battery ages.

In an embodiment, the battery has an off voltage below which the therapy module of the implantable medical device may cease to operate properly, wherein the implantable medical device has a patient recharge compliance period commencing upon the action and ending when the voltage of the battery reaches the off voltage and wherein the recharge voltage is varied in order to tend to equalize an amount of charge remaining in the battery during the patient recharge compliance period.

In an embodiment, the charge is maintained as approximately equal as the battery ages.

In an embodiment, the recharge voltage is varied in order that the patient recharge compliance period is maintained to be approximately equal as the battery ages.

In an embodiment, the recharge voltage is decreased in value as the battery ages in an early stage of a life of the battery and wherein the recharge voltage is increased in value as the battery ages in a later stage of the life of the battery.

In an embodiment, the recharge voltage is increased in value as the battery ages in an early stage of a life of the battery and wherein the recharge voltage is decreased in value as the battery ages in a later stage of the life of the battery.

DRAWINGS

Figure 13:
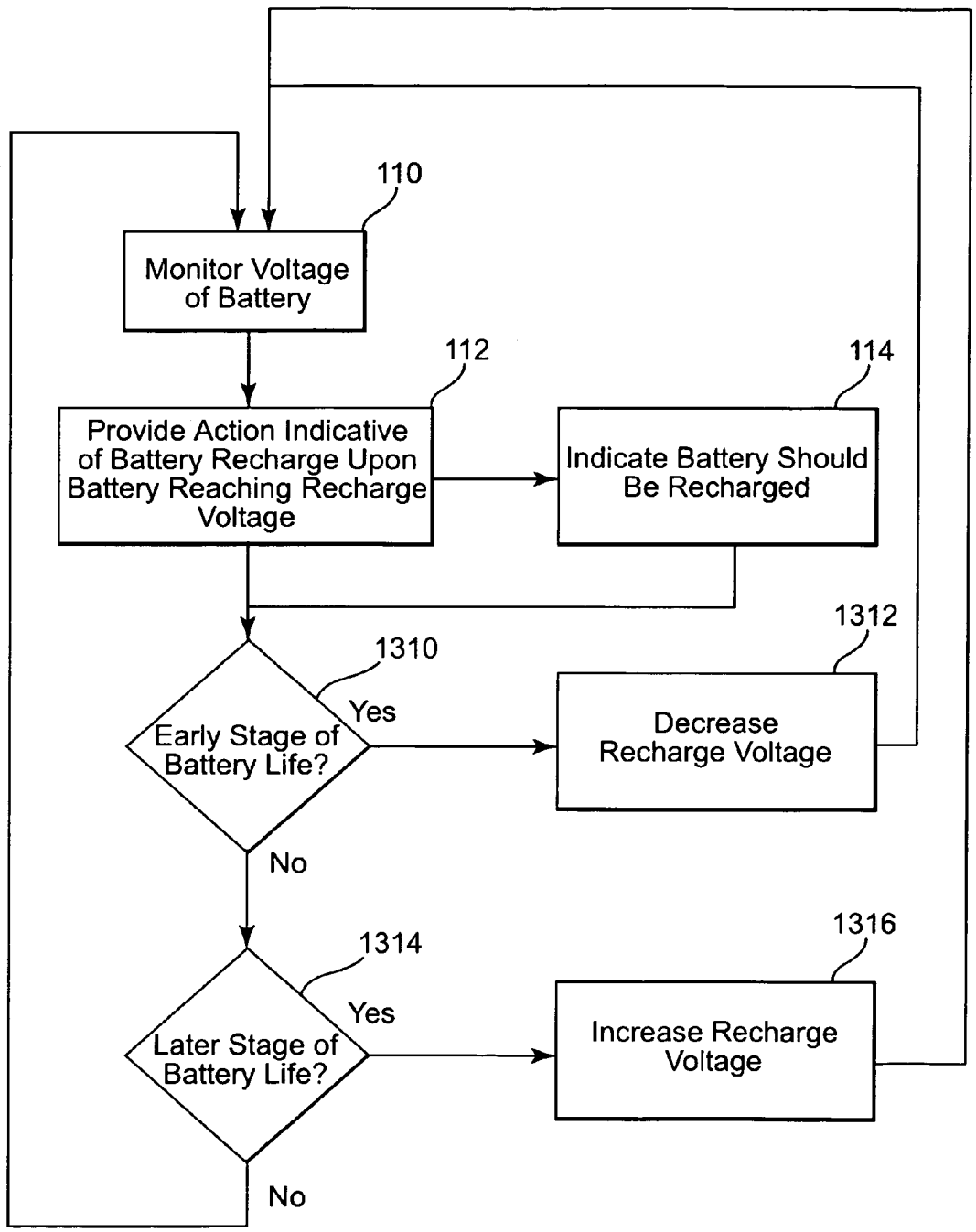
Figure 14:
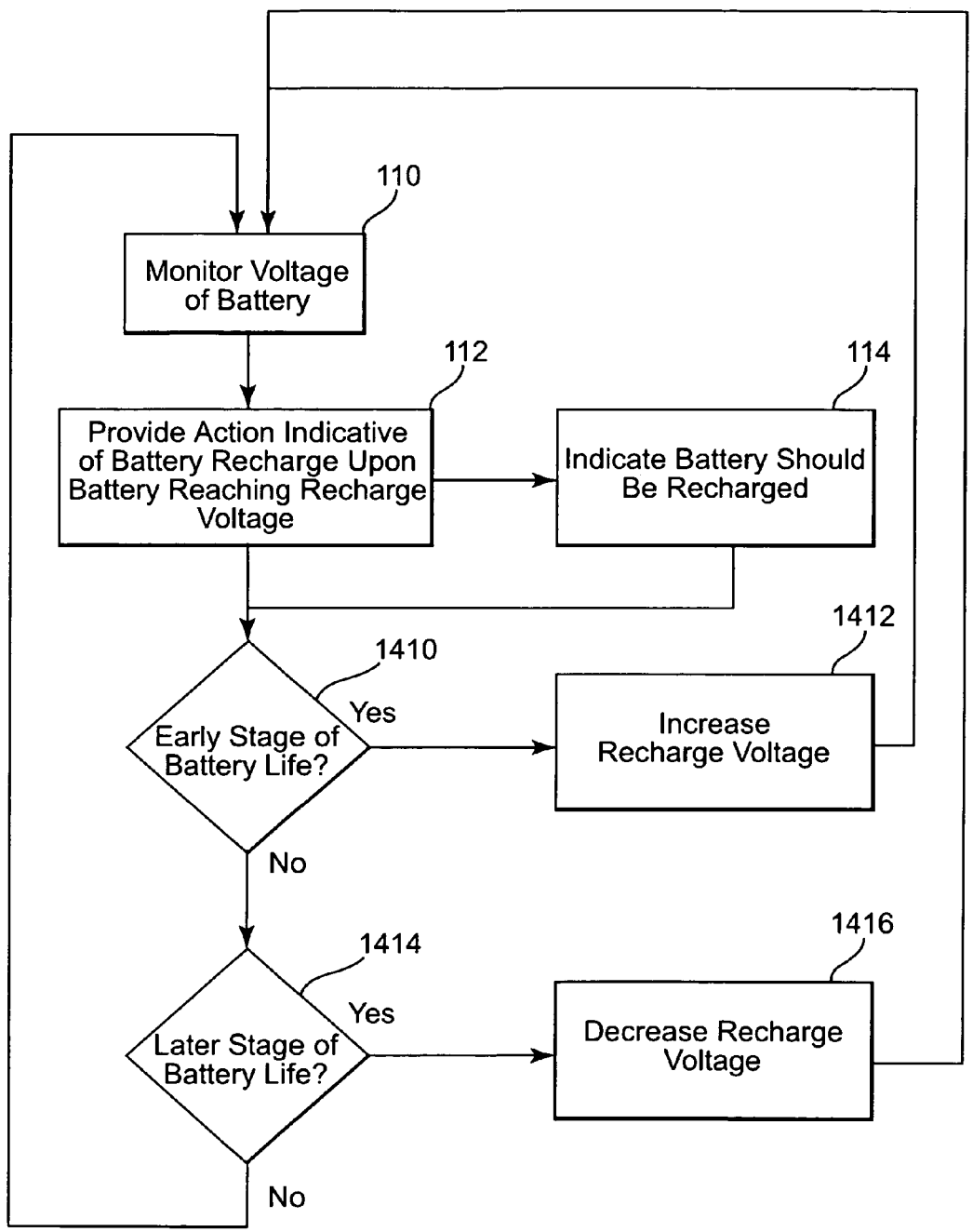

FIG. 13 is a flow diagram illustrating decreasing the recharge voltage during an early stage of life of the battery of an implantable medical device and increasing the recharge voltage during a later stage of life of the battery of an implantable medical device; and FIG. 14 is a flow diagram illustrating increasing the recharge voltage during an early stage of life of the battery of an implantable medical device and decreasing the recharge voltage during a later stage of the life of the battery of an implantable medical device.

DETAILED DESCRIPTION

The entire contents of U.S. Pat. No. 6,820,019, Kelly et al, Device and Method For Determining and Communicating the Remaining Life of a Battery in an Implantable Neurological Tissue Stimulating Device, filed Jul. 31, 1999, issued Nov. 16, 2004, is hereby incorporated by reference.

The entire contents of U.S. patent application Ser. No. 09/562,221, Torgerson et al, Battery Recharge Management For an Implantable Medical Device, filed Apr. 28, 2000, is hereby incorporated by reference.

Figure 1:
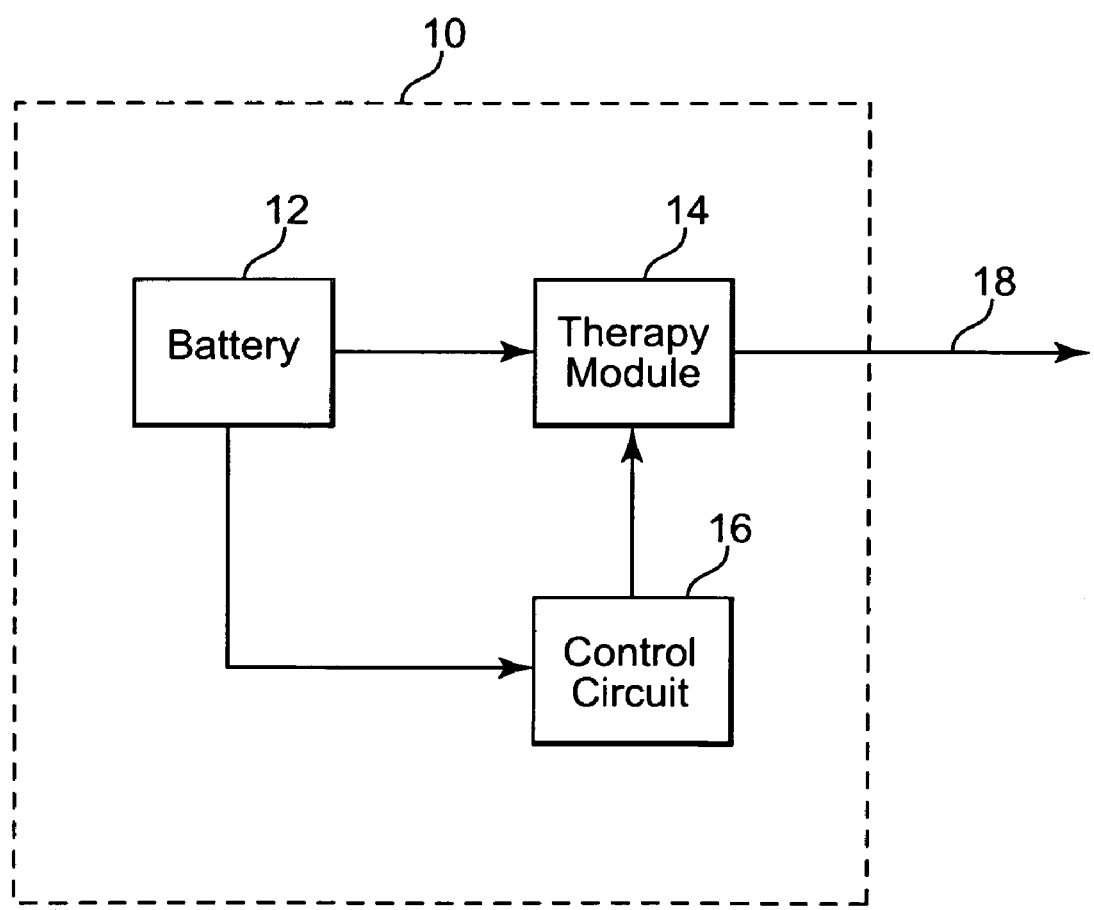
FIG. 1 is a block diagram of an implantable medical device.

FIG. 1 is a block diagram of implantable medical device 10. Implantable medical device 10 is powered by battery 12 driving both therapy module 14 and control circuit 16. Therapy module 14 is conventional and produces a therapeutic output 18. Examples of therapeutic output 18 include, but are not limited to, therapeutic substance infusion and/or electrical stimulation. Battery 12 is also a rechargeable battery and is conventional. Examples of battery chemistries include, but are not limited to, lithium ion, lithium polymer, nickel cadmium and nickel metal hydride.

Control circuit 16 may be conventional except as it relates to controlling operation and/or response to changing battery voltages and conditions as described below. In general, control circuit 16 may consist of a general purpose microprocessor programmed in order to accomplish the tasks identified below. In addition to those tasks identified below, control circuit 16 may perform conventional command, control and communication functions commonly associated with implantable medical devices.

Figure 2:
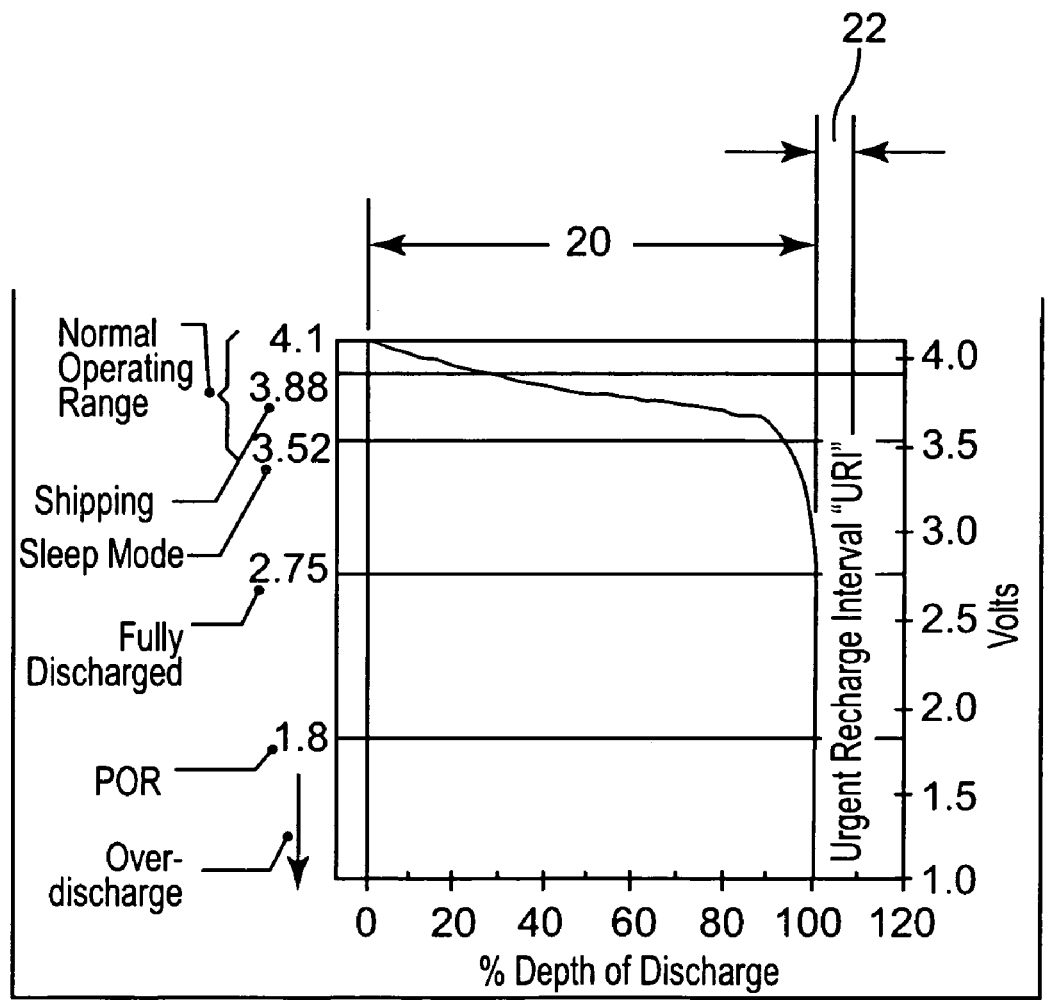
FIG. 2 illustrates a voltage versus percent of depth of discharge of an exemplary battery for an implantable medical device illustrating particular voltages ranges.

FIG. 2 is a graphical illustration of the voltage of battery 12 versus percent depth of discharge. While the graph of FIG. 2 is illustrated in terms of percent of discharge, it is to be recognized and understood that the graph also generally represents an illustration of battery voltage versus time since over time the percent of discharge of battery 12 will increase.

As shown in FIG. 2, a fully charged, i.e., zero percent (0%) discharged, battery 12 has a voltage of approximately 4.1 volts. The voltage of battery 12 gradually discharges generally linearly during operation of implantable medical device 10 until reaching approximately the ninety percent (90%) discharge point on the curve. At this point, battery 12 has a voltage of approximately 3.6 volts. As battery 12 continues to discharge from ninety percent (90%) toward one hundred percent (100%) discharge, the voltage of battery 12 drops significantly. The normal operating range of battery 12 is from a fully charged 4.1 volts to approximately 3.52 volts, at approximately the ninety percent (90%) discharged point in time, also known as the recharge voltage or therapy off voltage.

The recharge interval, or the operational period 20, is the time period between the fully charged 4.1 volts, zero percent (0%) discharged, point to the 3.52 volts, recharge voltage, approximately ninety percent (90%) discharged, point.

The patient compliance period 22 is measured from the 3.52 volt recharge voltage, approximately ninety percent (90%) discharged, point to the POR voltage, or power-on-reset voltage, of 1.8 volts, approaching one hundred percent (100%) discharged. Below 1.8 volts, operation of implantable medical device 10 may not be assured. Thus, the patient should have battery 12 recharged at least by the end of the patient compliance period 22.

Figure 3:
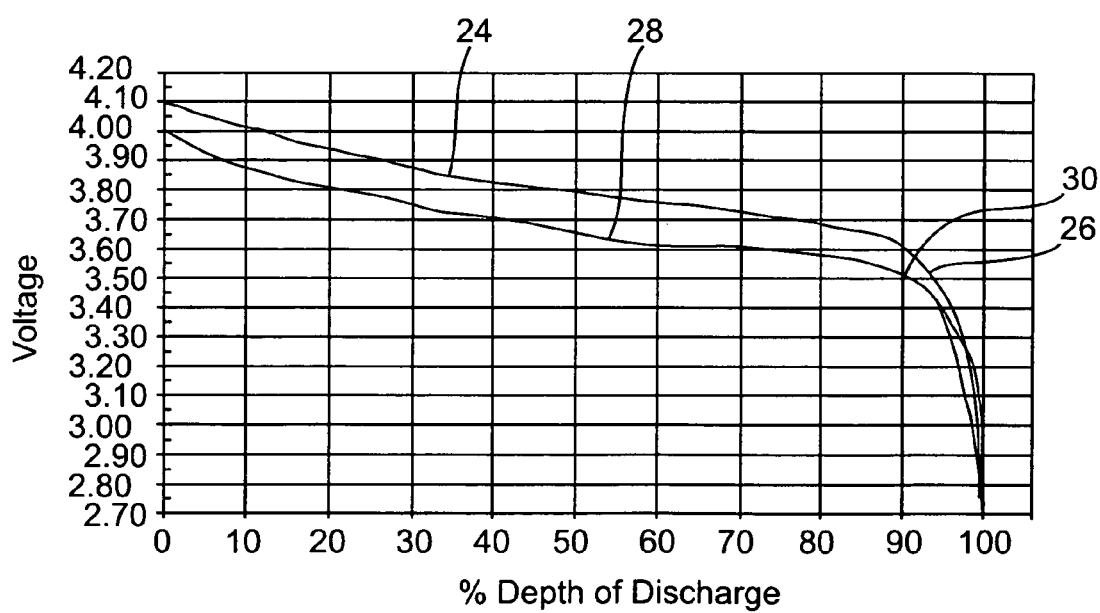
FIG. 3 illustrates a voltage versus percent of depth of discharge of an exemplary battery for an implantable medical device.

As battery 12 ages and its operational characteristics fade over time, the patient compliance period 22 between the recharge voltage of 3.52 volts and the POR voltage of 1.8 volts decreases. This effect is illustrated by referring to the illustration of FIG. 3. Curve 24 in FIG. 3 illustrates the voltage discharge characteristics of an exemplary new battery 12. As shown in FIG. 2, new battery 12 has a fully charged voltage of 4.1 volts and a recharge voltage of 3.52 volts at point 26. As battery 12 ages, battery 12 will not quite reach a fully charged voltage of 4.1 volts but the fully charged voltage of an aged battery 12 may be somewhat less, perhaps 4.0 volts as shown by curve 28. Curve 28 illustrates that the recharge voltage of 3.52 volts will be reached earlier at point 30 resulting in a shorter operational period. Similarly, the time period between recharge voltage and POR voltage for curve 28 representing an aged battery 12 is also shorter.

Lithium ion battery chemistry has fade, i.e., aging, characteristics that can be split into two fade mechanisms. The first, calendar fade, is approximately six percent (6%) per year and is generally constant over the life of the battery. The second, cycle fade, is approximately 0.003 percent (0.003%) per year based upon normal usage and occurs each time battery 12 is fully discharged. These two fade characteristics help determine how recharge voltage should be varied to improve the operation of implantable medical device 10.

Since calendar fade can be approximately six percent (6%) per year, recharge voltage can be decreased by a specific amount over time, e.g., by decreasing the recharge voltage by about six percent (6%) every year. This decrease could be done at a single time each year or it could be split up into an interval of 0.5% per month or any other interval.

In a patient recharged implantable medical device 10 approximately once per week, battery 12 would be recharged approximately fifty-two (52) times each year resulting in an additional 0.16% of cycle fade every year. For this example, recharge voltage could be reduced by approximately 6.16% per year to account for both calendar fade and cycle fade.

Further, implantable medical device 10 could keep track of the number of recharge cycles encountered and adjust the recharge voltage based upon the actual number of recharge cycles. If the patient recharges battery 12 of implantable medical device daily, the recharge voltage could change more quickly to account for the additional cycle fade. Cycles could be calculated by using therapy settings and the battery capacity or the amount of time spent charging battery 12 and the battery capacity, for example.

These adjustments decrease the recharge voltage over time as battery 12 ages in order to tend to maintain the operational period 20 of implantable medical device 10 over time. Maintaining operational period 20 relatively constant over time provides an implantable medical device 10 that is more consistent and easier to operate since recharging won't be required at increasingly shorter intervals.

Recharge voltage may also be varied by increasing the recharge voltage over time as battery 12 ages. As battery 12 ages, the patient compliance period 22 also decreases. A decreasing patient compliance period 22 may be problematic as patients have a shorter and shorter time in which to recharge battery 12 once receiving a recharge warning. Increasing the recharge voltage over time as battery 12 ages would tend to maintain the patient compliance period 22 over time and enable the patient to have a consistent time over which to recharge battery 12. A consistent patient compliance period 22 may provide the patient with enough time to recharge battery 12 before battery 12 is damaged or implantable medical device 10 ceases to function. This may be important even if battery 12 is zero-volt compliant and is not damaged since implantable medical device 10 may enter POR and could not communicate until battery 12 is charged to a certain level. Implantable medical device 10 may lose settings stored in volatile memory and would not be able to communicate until battery 12 is charged to a certain level.

As above, recharge voltage could be done at a constant rate or could be increased as a function of the number recharge cycles to which battery 12 is subjected.

Figure 4:
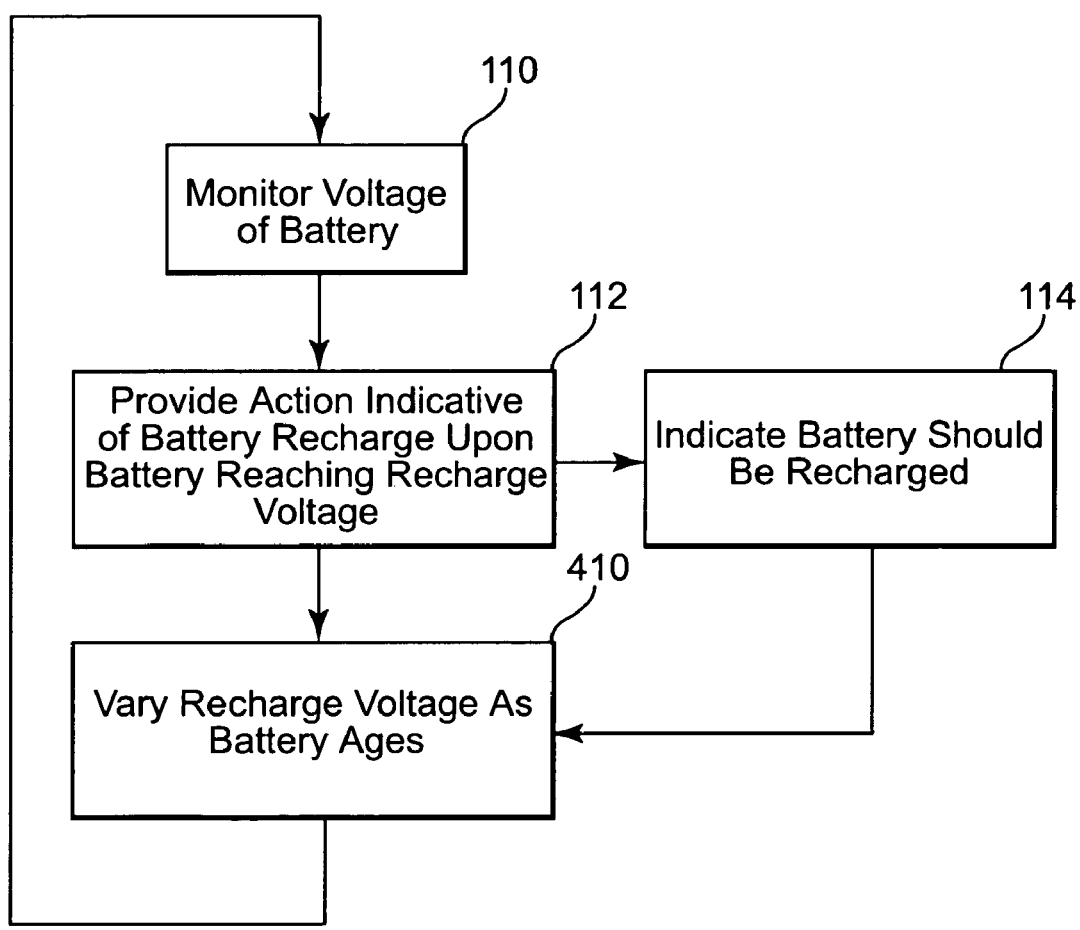
FIG. 4 is a flow diagram illustrating varying the recharge voltage as the battery of an implantable medical device ages.

FIG. 4 is a flow chart illustrating an embodiment of the invention. The voltage of battery 12 in monitored (110). An action indicative of battery recharge is initiated (112) when the voltage of battery 12 reaches the recharge voltage. As an example, an alarm or other indication could be issued (114) warning the user that battery 12 should be recharged. The patient would know that implantable medical device is then entering the patient compliance period 22. The recharge voltage is then varied (410) to account for aging of battery 12 over time. Such variation of the recharge voltage could be as described above or differently in order to alter the operational period 20 and/or patient compliance period 22 of implantable medical device 10.

Figure 5:
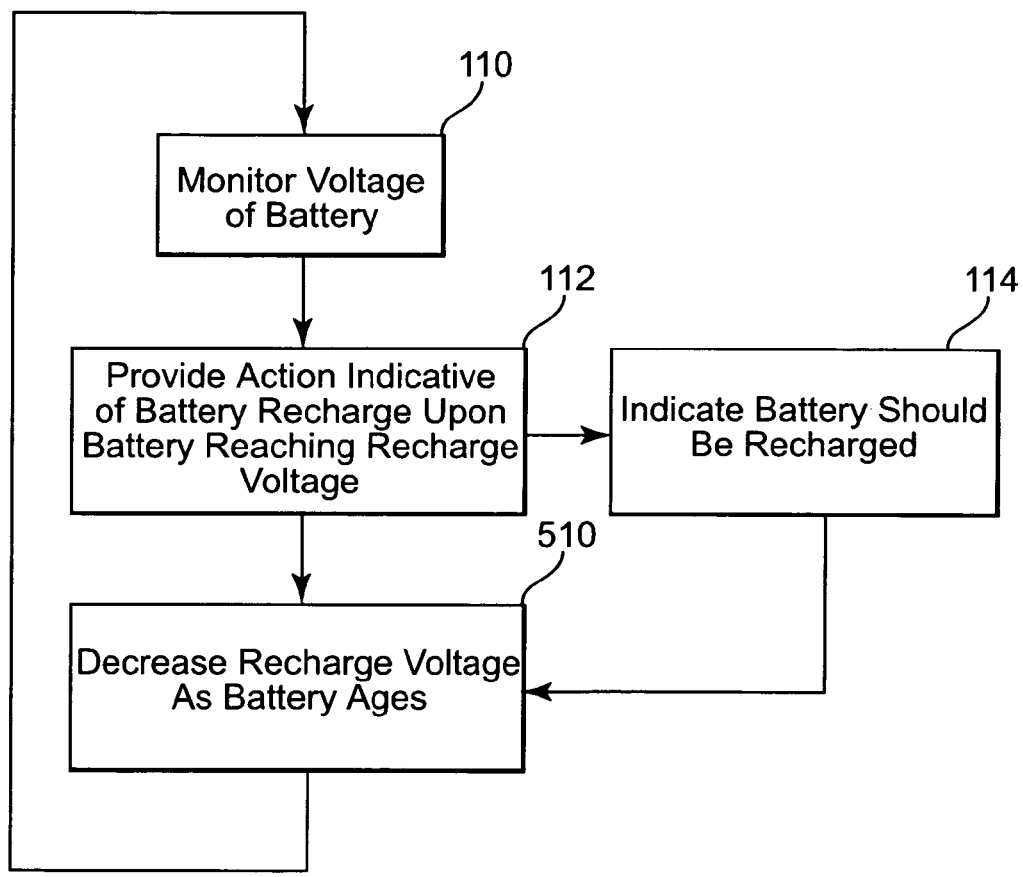
FIG. 5 is a flow diagram illustrating decreasing the recharge voltage as the battery of an implantable medical device ages.

FIG. 5 is a flow chart illustrating an embodiment of the invention. The voltage of battery 12 in monitored (110). An action indicative of battery recharge is initiated (112) when the voltage of battery 12 reaches the recharge voltage. As an example, an alarm or other indication could be issued (114) warning the user that battery 12 should be recharged. The patient would know that implantable medical device is then entering the patient compliance period 22. The recharge voltage is then decreased (510) to account for aging of battery 12 over time. Decreasing the recharge voltage over time will tend to maintain operational period 20. In an embodiment, the recharge voltage is decreased to maintain operational period 20 of implantable medical device 10 approximately constant.

Figure 6:
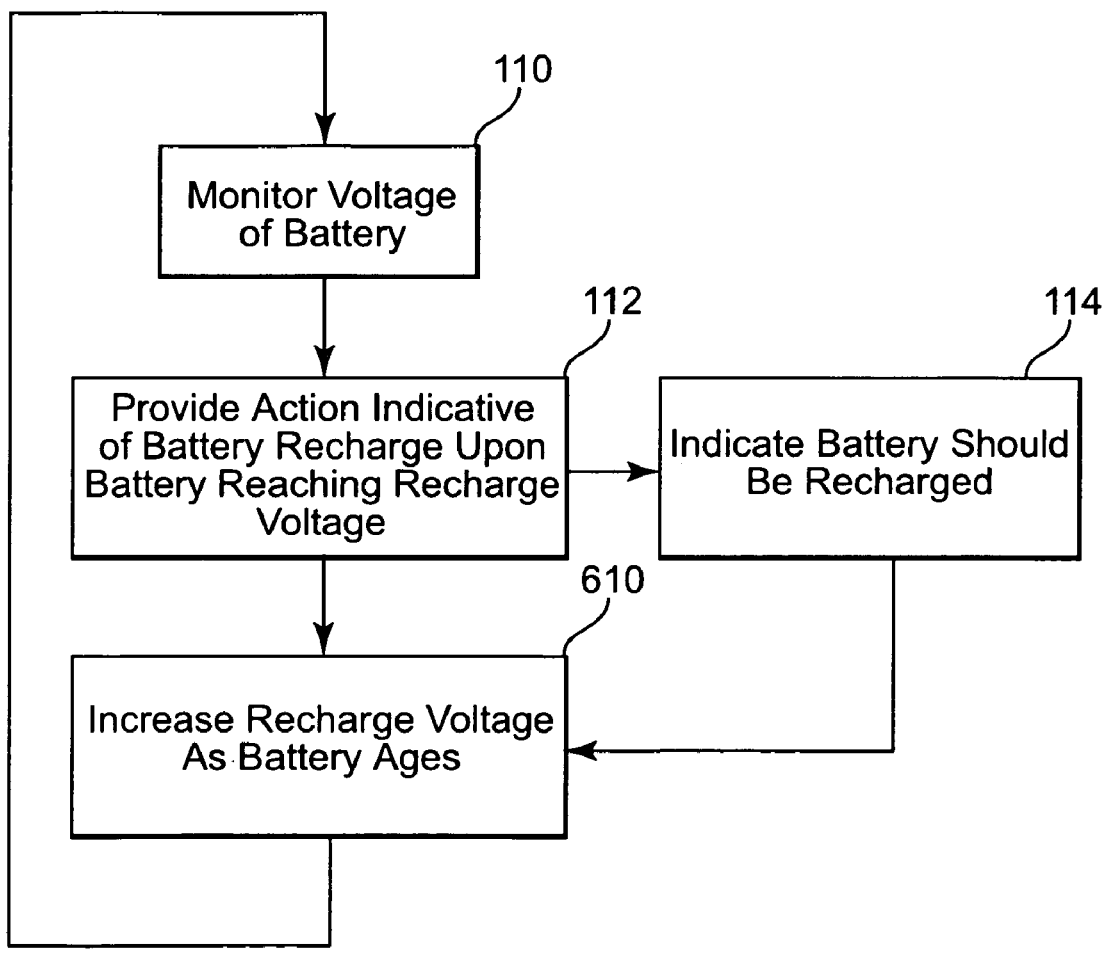
FIG. 6 is a flow diagram illustrating increasing the recharge voltage as the battery of an implantable medical device ages.

FIG. 6 is a flow chart illustrating an embodiment of the invention. The voltage of battery 12 in monitored (110). An action indicative of battery recharge is initiated (112) when the voltage of battery 12 reaches the recharge voltage. As an example, an alarm or other indication could be issued (114) warning the user that battery 12 should be recharged. The patient would know that implantable medical device is then entering the patient compliance period 22. The recharge voltage is then increased (610) to account for aging of battery 12 over time. Increasing the recharge voltage over time will tend to maintain patient compliance period 22. In an embodiment, the recharge voltage is increased to maintain patient compliance period 22 of implantable medical device 10 approximately constant.

Figure 7:
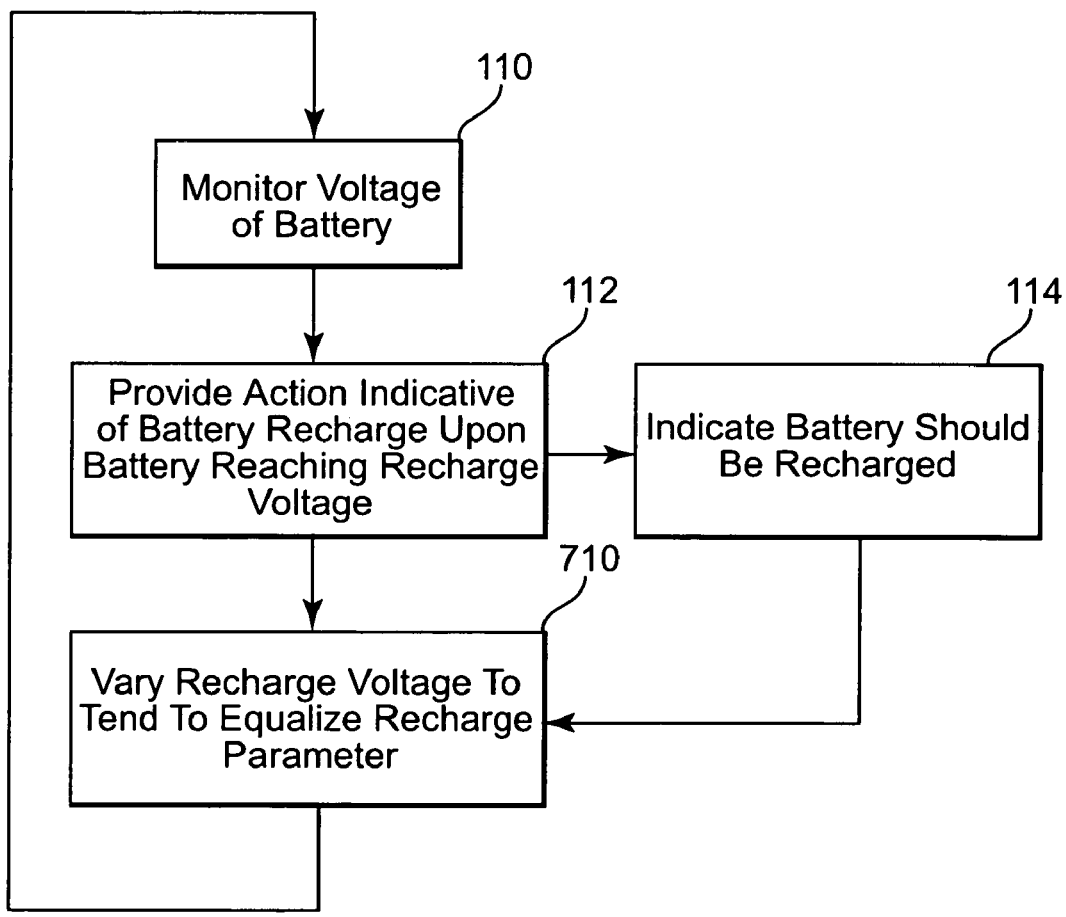
FIG. 7 is a flow diagram illustrating varying the recharge voltage of the battery of an implantable medical device in order to tend to equalize a recharge parameter.

FIG. 7 is a flow chart illustrating an embodiment of the invention. The voltage of battery 12 in monitored (110). An action indicative of battery recharge is initiated (112) when the voltage of battery 12 reaches the recharge voltage. As an example, an alarm or other indication could be issued (114) warning the user that battery 12 should be recharged. The patient would know that implantable medical device is then entering the patient compliance period 22. The recharge voltage is then varied (710) to tend to equalize a recharge parameter. Recharge parameters that may tend to be equalized include, but are not limited to, the operational period 20 and/or the patient compliance period 22. In an embodiment, the recharge voltage is varied to maintain a recharge parameter of implantable medical device 10 approximately constant.

Figure 8:
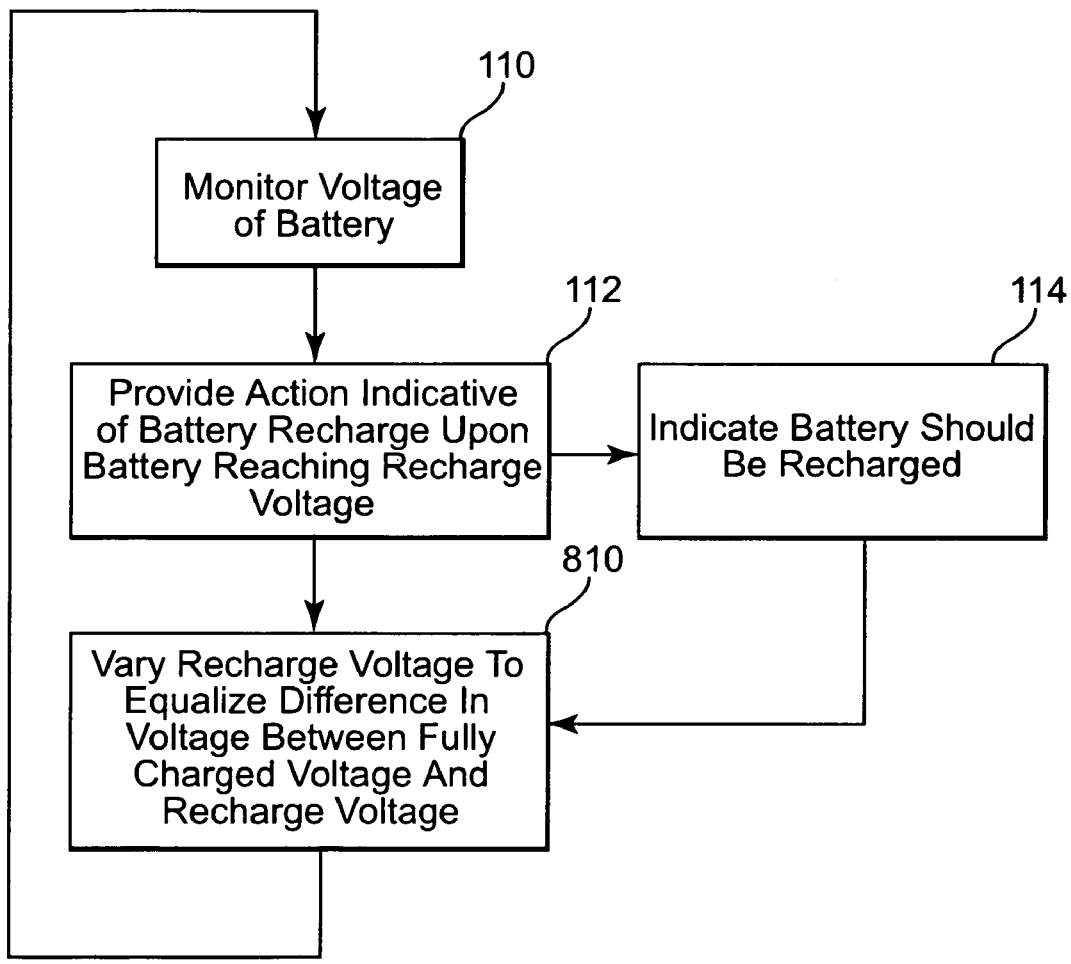
FIG. 8 is a flow diagram illustrating varying the recharge voltage of the battery of an implantable medical device in order to tend to equalize the difference between the voltage of a fully charged battery and the recharge voltage.

FIG. 8 is a flow chart illustrating an embodiment of the invention. The voltage of battery 12 in monitored (110). An action indicative of battery recharge is initiated (112) when the voltage of battery 12 reaches the recharge voltage. As an example, an alarm or other indication could be issued (114) warning the user that battery 12 should be recharged. The patient would know that implantable medical device is then entering the patient compliance period 22. The recharge voltage is then varied (810) to tend to equalize the difference in voltage between a fully charged voltage of battery 12 and the recharge voltage of battery 12. In an embodiment, the recharge voltage is varied to maintain the difference in voltage between a fully charged voltage of battery 12 and the recharge voltage of battery 12.

Figure 9:
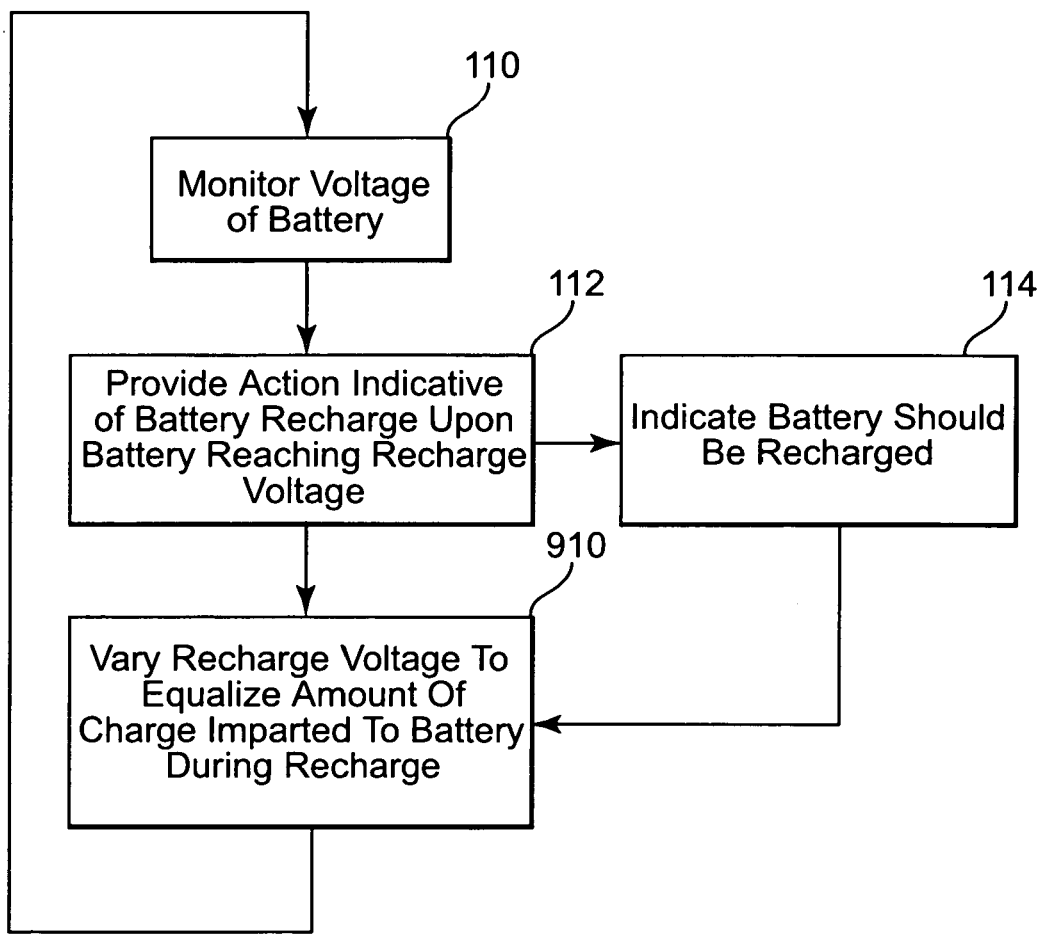
FIG. 9 is a flow diagram illustrating varying the recharge voltage of the battery of an implantable medical device in order to tend to equalize the amount of charge imparted to the battery during recharge.

FIG. 9 is a flow chart illustrating an embodiment of the invention. The voltage of battery 12 in monitored (110). An action indicative of battery recharge is initiated (112) when the voltage of battery 12 reaches the recharge voltage. As an example, an alarm or other indication could be issued (114) warning the user that battery 12 should be recharged. The patient would know that implantable medical device is then entering the patient compliance period 22. The recharge voltage is then varied (910) to tend to equalize the amount of charge imparted to battery 12 during recharge. In an embodiment, the recharge voltage is varied to maintain the amount of charge imparted to battery 12 during recharge.

Figure 10:
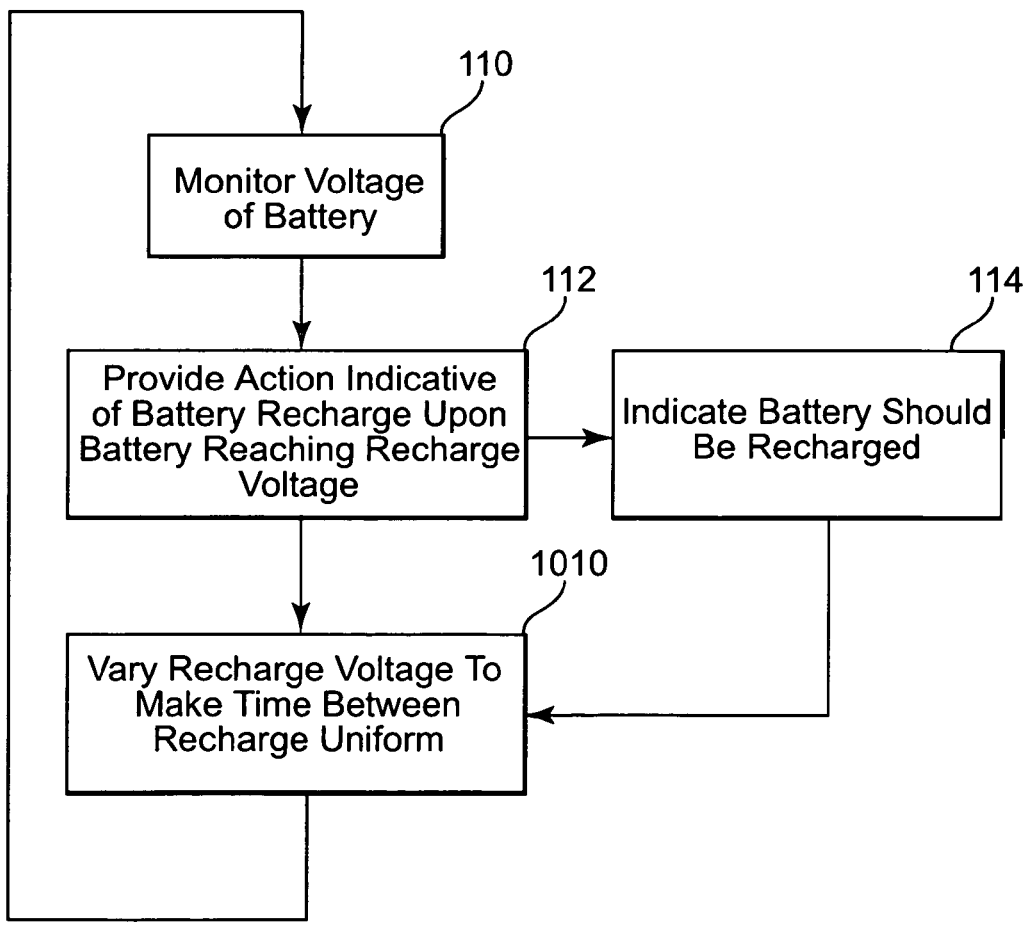
FIG. 10 is a flow diagram illustrating varying the recharge voltage of the battery of an implantable medical device in order to tend to make the time between recharge more uniform.

FIG. 10 is a flow chart illustrating an embodiment of the invention. The voltage of battery 12 in monitored (110). An action indicative of battery recharge is initiated (112) when the voltage of battery 12 reaches the recharge voltage. As an example, an alarm or other indication could be issued (114) warning the user that battery 12 should be recharged. The patient would know that implantable medical device is then entering the patient compliance period 22. The recharge voltage is then varied (1010) to tend to equalize the time between recharge cycles of implantable medical device 10. This is similar to maintaining the operational period 20. In an embodiment, the recharge voltage is varied to maintain the time between recharge cycles of implantable medical device 10.

Figure 11:
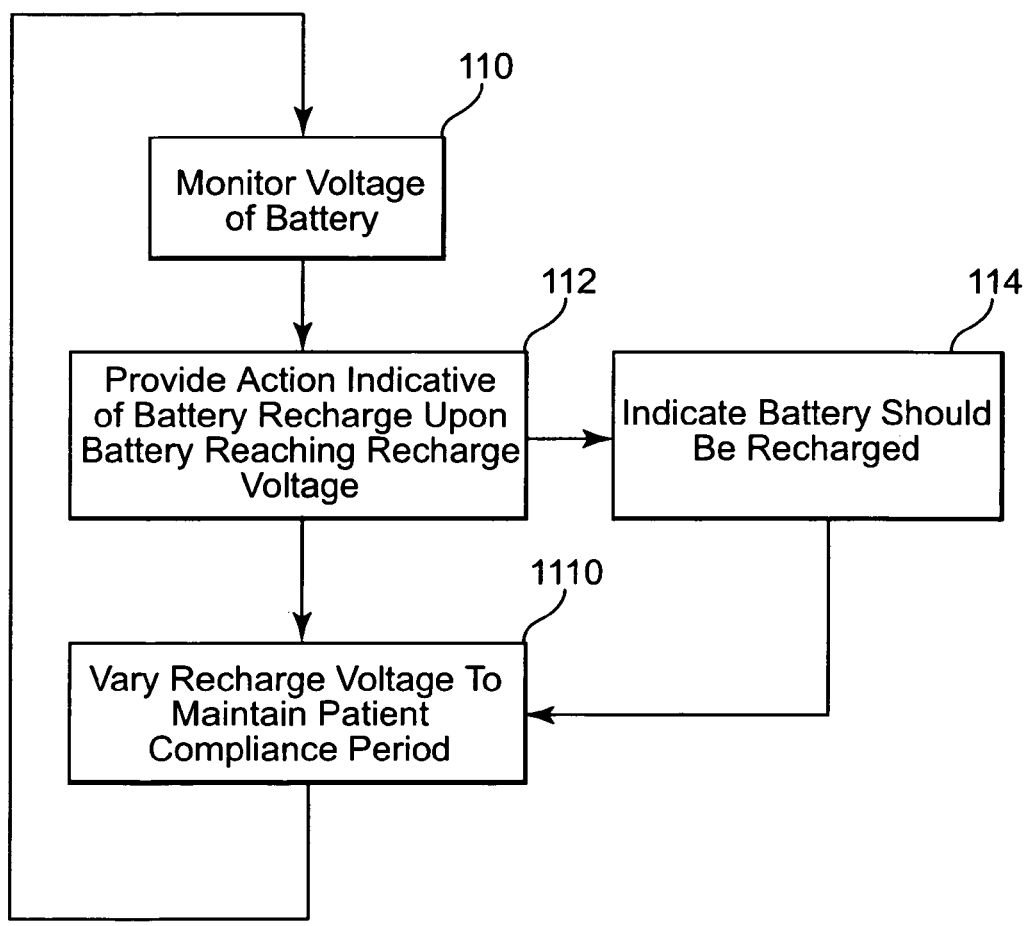
FIG. 11 is a flow diagram illustrating varying the recharge voltage of the battery of an implantable medical device in order to tend to maintain the patient compliance period.

FIG. 11 is a flow chart illustrating an embodiment of the invention. The voltage of battery 12 in monitored (110). An action indicative of battery recharge is initiated (112) when the voltage of battery 12 reaches the recharge voltage. As an example, an alarm or other indication could be issued (114) warning the user that battery 12 should be recharged. The patient would know that implantable medical device is then entering the patient compliance period 22. The recharge voltage is then varied (1110) to tend to equalize the patient compliance period 22. In an embodiment, the recharge voltage is varied to maintain the patient compliance period 22.

Figure 12:
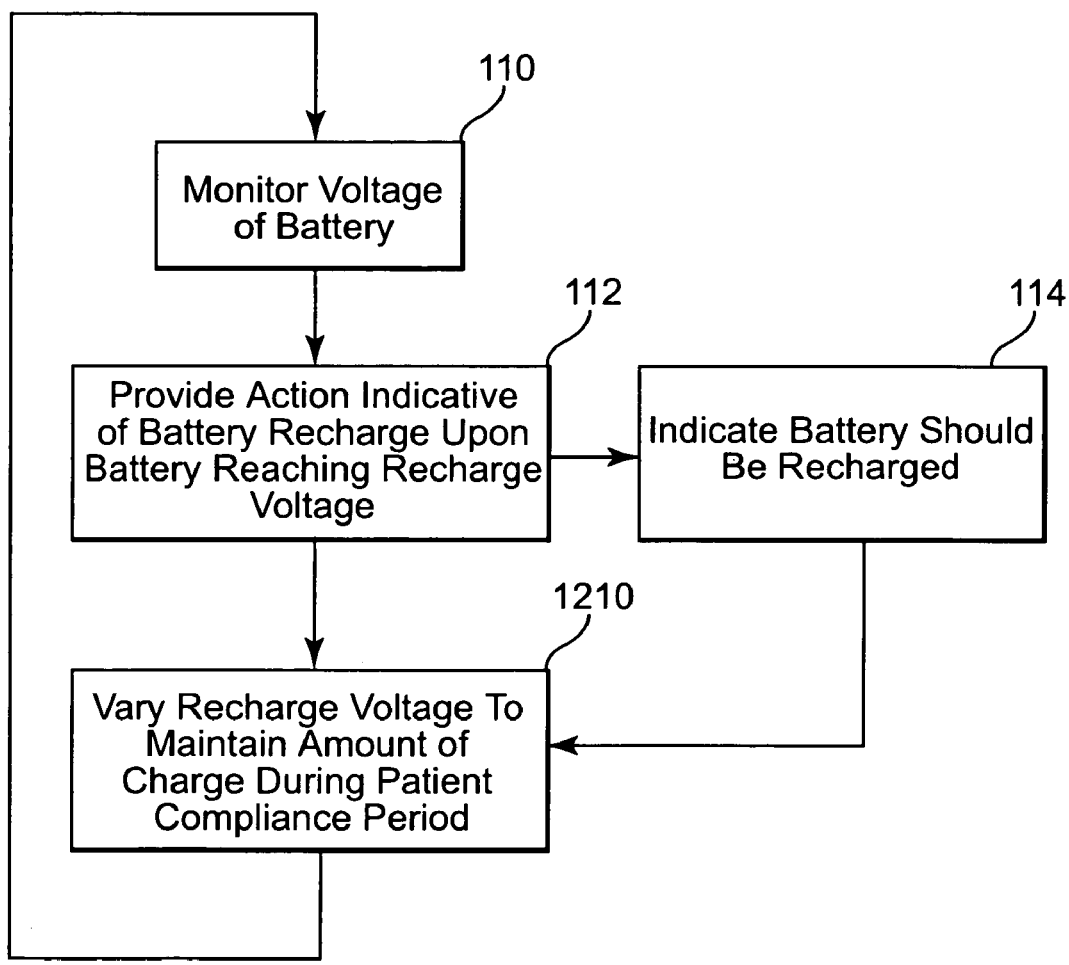
FIG. 12 is a flow diagram illustrating varying the recharge voltage of the battery of an implantable medical device in order to tend to maintain an amount of charge in the battery during the patient compliance period.

FIG. 12 is a flow chart illustrating an embodiment of the invention. The voltage of battery 12 in monitored (110). An action indicative of battery recharge is initiated (112) when the voltage of battery 12 reaches the recharge voltage. As an example, an alarm or other indication could be issued (114) warning the user that battery 12 should be recharged. The patient would know that implantable medical device is then entering the patient compliance period 22. The recharge voltage is then varied (1210) to tend to maintain the amount of charge remaining in battery 12 during the patient compliance period 22. In an embodiment, the recharge voltage is varied to maintain the amount of charge remaining in battery 12 during the patient compliance period 22.

FIG. 13 is a flow chart illustrating an embodiment of the invention. The voltage of battery 12 in monitored (110). An action indicative of battery recharge is initiated (112) when the voltage of battery 12 reaches the recharge voltage. As an example, an alarm or other indication could be issued (114) warning the user that battery 12 should be recharged. The patient would know that implantable medical device is then entering the patient compliance period 22. If (1310) battery 12 is in an early stage of battery life, e.g., battery 12 is relatively new, then the recharge voltage is decreased (1312) in order to tend to maintain operational period 20. However, as battery 12 ages and patient compliance period 22 becomes increasingly shorter, there may come a time during the life of battery 12 that maintaining the patient compliance period 22 may become more important than maintaining the operational period 20. If then (1314) battery 12 is in a later stage of battery life, e.g., battery 12 is relatively used, then the recharge voltage is increased (1316) in order to tend to maintain patient compliance period 22.

FIG. 14 is a flow chart illustrating a converse embodiment of the invention. The voltage of battery 12 in monitored (110). An action indicative of battery recharge is initiated (112) when the voltage of battery 12 reaches the recharge voltage. As an example, an alarm or other indication could be issued (114) warning the user that battery 12 should be recharged. The patient would know that implantable medical device is then entering the patient compliance period 22. If (1410) battery 12 is in an early stage of battery life, e.g., battery 12 is relatively new, then the recharge voltage is increased (1412) in order to tend to maintain patient compliance period 22. However, as battery 12 ages and operational period 20 becomes increasingly shorter, there may come a time during the life of battery 12 that maintaining the operational period 20 may become more important than maintaining the patient compliance period 22. If then (1414) battery 12 is in a later stage of battery life, e.g., battery 12 is relatively used, then the recharge voltage is decreased (1416) in order to tend to maintain operational period 20.

The above description may cover only some of the possible ways in which the recharge voltage may be varied in order to advantageously alter the operational characteristics of implantable medical device 10. It is to be recognized and understood that the recharge voltage may be varied in other ways within the contemplation of the present invention in order to alter operational characteristics of implantable medical device 10 in other ways.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device adapted to provide a therapeutic output to a patient, comprising:
    a battery having a voltage;
    a therapy module, operatively coupled to said battery, adapted to provide said therapeutic output;
    a control circuit, operatively coupled to said battery, providing an action indicative of recharging said battery when said voltage of said battery discharges to a recharge voltage;
    wherein said recharge voltage is varied as said battery ages;
    wherein said recharge voltage is decreased in value as said battery ages.

2. An implantable medical device as in claim 1 wherein said action comprises indicating that said battery should be recharged.

3. An implantable medical device adapted to provide a therapeutic output to a patient, comprising:
    a battery having a voltage;
    a therapy module, operatively coupled to said battery, adapted to provide said therapeutic output;
    a control circuit, operatively coupled to said battery, providing an action indicative of recharging said battery when said voltage of said battery discharges to a recharge voltage;
    wherein said recharge voltage is varied as said battery ages;
    wherein said battery has a fully charged capacity that declines as said battery ages and wherein said recharge voltage is varied in order to tend to equalize a value of a difference in voltage between a fully charged voltage and said recharge voltage as said battery ages.

4. An implantable medical device as in claim 3 wherein said difference is maintained to be approximately equal.

5. An implantable medical device adapted to provide a therapeutic output to a patient, comprising:
   a battery having a voltage;
   a therapy module, operatively coupled to said battery, adapted to provide said therapeutic output;
   a control circuit, operatively coupled to said battery, providing an action indicative of recharging said battery when said voltage of said battery discharges to a recharge voltage;
   wherein said recharge voltage is varied as said battery ages;
   wherein said battery has a fully charged capacity that declines as said battery ages and wherein said recharge voltage is varied in order to tend to equalize an amount of charge imparted to said battery during recharge between a fully charged voltage and said recharge voltage.

6. An implantable medical device as in claim 5 wherein said charge is maintained as approximately equal as said battery ages.

7. An implantable medical device adapted to provide a therapeutic output to a patient, comprising:
   a battery having a voltage;
   a therapy module, operatively coupled to said battery, adapted to provide said therapeutic output;
   a control circuit, operatively coupled to said battery, providing an action indicative of recharging said battery when said voltage of said battery discharges to a recharge voltage;
   wherein said recharge voltage is varied as said battery ages;
   wherein said voltage is varied such that a time between a first recharge of said battery and a second recharge of said battery is made more uniform as said battery ages.

8. An implantable medical device as in claim 7 wherein said time is approximately equal.

9. An implantable medical device adapted to provide a therapeutic output to a patient, comprising:
   a battery having a voltage;
   a therapy module, operatively coupled to said battery, adapted to provide said therapeutic output;
   a control circuit, operatively coupled to said battery, providing an action indicative of recharging said battery when said voltage of said battery discharges to a recharge voltage;
   wherein said recharge voltage is varied as said battery ages;
   wherein said recharge voltage is decreased in value as said battery ages in an early stage of a life of said battery and wherein said recharge voltage is increased in value as said battery ages in a later stage of said life of said battery.

10. An implantable medical device adapted to provide a therapeutic output to a patient, comprising:
    a battery having a voltage;
    a therapy module, operatively coupled to said battery, adapted to provide said therapeutic output;
    a control circuit, operatively coupled to said battery, providing an action indicative of recharging said battery when said voltage of said battery discharges to a recharge voltage;
    wherein said recharge voltage is varied as said battery ages,
    wherein said recharge voltage is increased in value as said battery ages in an early stage of a life of said battery and wherein said recharge voltage is decreased in value as said battery ages in a later stage of said life of said battery.

11. A method of providing a therapeutic output to a patient using an implantable medical device having a battery having a voltage, comprising:
    providing an action indicative of recharging said battery when said voltage of said battery discharges to a recharge voltage; and
    varying said recharge voltage as said battery ages;
    wherein said recharge voltage in said varying step is decreased in value as said battery ages.

12. A method of providing a therapeutic output to a patient using an implantable medical device having a battery having a voltage, comprising:
    providing an action indicative of recharging said battery when said voltage of said battery discharges to a recharge voltage; and
    varying said recharge voltage as said battery ages;
    wherein said battery has a fully charged capacity that declines as said battery ages and wherein said recharge voltage is varied in order to tend to equalize a value of a difference in voltage between a fully charged voltage and said recharge voltage as said battery ages.

13. A method as in claim 12 wherein said difference is maintained to be approximately equal.

14. A method of providing a therapeutic output to a patient using an implantable medical device having a battery having a voltage, comprising:
    providing an action indicative of recharging said battery when said voltage of said battery discharges to a recharge voltage; and
    varying said recharge voltage as said battery ages;
    wherein said battery has a fully charged capacity that declines as said battery ages and wherein said recharge voltage is varied in order to tend to equalize an amount of charge imparted to said battery during recharge between a fully charged voltage and said recharge voltage.

15. A method as in claim 14 wherein said charge is maintained as approximately equal as said battery ages.

16. A method of providing a therapeutic output to a patient using an implantable medical device having a battery having a voltage, comprising:
    providing an action indicative of recharging said battery when said voltage of said battery discharges to a recharge voltage; and
    varying said recharge voltage as said battery ages;
    wherein said voltage is varied such that a time between a first recharge of said battery and a second recharge of said battery is made more uniform as said battery ages.

17. A method as in claim 16 wherein said time is approximately equal.

18. A method as in claim 16 wherein said action step comprises indicating that said battery should be recharged.

19. A method of providing a therapeutic output to a patient using an implantable medical device having a battery having a voltage, comprising:
    providing an action indicative of recharging said battery when said voltage of said battery discharges to a recharge voltage; and
    varying said recharge voltage as said battery ages;
    wherein said recharge voltage is decreased in value as said battery ages in an early stage of a life of said battery and wherein said recharge voltage is increased in value as said battery ages in a later stage of said life of said battery.

20. A method of providing a therapeutic output to a patient using an implantable medical device having a battery having a voltage, comprising:

providing an action indicative of recharging said battery when said voltage of said battery discharges to a recharge voltage; and varying said recharge voltage as said battery ages;

wherein said recharge voltage is increased in value as said battery ages in an early stage of a life of said battery and wherein said recharge voltage is decreased in value as said battery ages in a later stage of said life of said battery.

21. An implantable medical device adapted to provide a therapeutic output to a patient, comprising:

a battery having a voltage;

a therapy module, operatively coupled to said battery, adapted to provide said therapeutic output;

a control circuit, operatively coupled to said battery, including means for providing an action indicative of recharging said battery when said voltage of said battery discharges to a recharge voltage;

wherein said means includes means for varying the recharge voltage as said battery ages;

wherein the means for varying the recharge voltage as said battery ages includes means for decreasing said recharge voltage in value as said battery ages in an early stage of a life of said battery and increasing said recharge voltage in value as said battery ages in a later stage of said life of said battery.

* * * * *

UNITED STATES PATENT AND TRADEMARK OFFICE
CERTIFICATE OF CORRECTION

| | | |
|---|---|---|
| PATENT NO. | : 7,616,995 B2 | Page 1 of 1 |
| APPLICATION NO. | : 11/414156 | |
| DATED | : November 10, 2009 | |
| INVENTOR(S) | : Wahlstrand et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 488 days.

Signed and Sealed this

Nineteenth Day of October, 2010

David J. Kappos
*Director of the United States Patent and Trademark Office*